(12) United States Patent
Vandewalle (10) Patent No.: US 8,715,293 B2
(45) Date of Patent: May 6, 2014

(54) METHOD AND APPARATUS FOR RETAINING A GUIDE WIRE

(75) Inventor: Mark V. Vandewalle, Pierceton, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1695 days.

(21) Appl. No.: 11/684,800

(22) Filed: Mar. 12, 2007

(65) Prior Publication Data

US 2007/0162046 A1  Jul. 12, 2007

Related U.S. Application Data

(62) Division of application No. 10/767,619, filed on Jan. 29, 2004, now Pat. No. 7,207,995.

(51) Int. Cl.
*A61B 17/56* (2006.01)

(52) U.S. Cl.
USPC ........................................ 606/104; 606/86 R (58) Field of Classification Search
USPC ............. 606/104, 103, 304, 86 R, 96; 81/451
See application file for complete search history.

(56) References Cited

U.S. PATENT DOCUMENTS

| | | | |
|---|---|---|---|
| 2,243,717 A | 5/1941 | Moreira | |
| 2,248,054 A * | 7/1941 | Becker | 81/457 |
| 2,631,584 A * | 3/1953 | Purificato | 606/68 |
| 3,718,340 A * | 2/1973 | Stewart | 279/57 |
| 4,124,026 A | 11/1978 | Berner et al. | |
| 4,587,963 A | 5/1986 | Leibinger et al. | |
| 5,071,420 A | 12/1991 | Paulos et al. | |
| 5,203,784 A | 4/1993 | Ross et al. | |
| 5,257,996 A | 11/1993 | McGuire | |
| 5,323,765 A | 6/1994 | Brown | |
| 5,391,170 A | 2/1995 | McGuire et al. | |
| 5,423,819 A | 6/1995 | Small et al. | |
| 5,429,641 A | 7/1995 | Gotfried | |
| 5,464,407 A | 11/1995 | McGuire | |
| 5,520,693 A | 5/1996 | McGuire et al. | |
| 5,658,289 A | 8/1997 | Boucher et al. | |
| 5,697,935 A | 12/1997 | Moran et al. | |
| 6,436,100 B1 | 8/2002 | Berger | |
| 6,827,722 B1 * | 12/2004 | Schoenefeld | 606/104 |

OTHER PUBLICATIONS

U.S. Appl. No. 10/767,619 (USPN 7,207,995).

* cited by examiner

*Primary Examiner* — Christian Sevilla
(74) *Attorney, Agent, or Firm* — Harness, Dickey (57) ABSTRACT

A cannulated medical instrument for insertion of a medical device over a guide wire generally includes a cannulated driver member configured to engage the medical device and insert the medical device at an insertion rate. A clasping device connects to the cannulated driver member. The clasping device moves the guide wire distally away from the cannulated driver member at an extraction rate upon rotation of the cannulated driver member.

25 Claims, 10 Drawing Sheets

METHOD AND APPARATUS FOR RETAINING A GUIDE WIRE

CROSS-REFERENCE TO RELATED APPLICATIONS

This application is a divisional of U.S. patent application Ser. No. 10/767,619 filed on Jan. 29, 2004 The disclosure of the above application is hereby incorporated by reference as if fully set forth herein.

FIELD

The present invention pertains generally to a guide wire capturing surgical instrument and, more particularly, to a cannulated guide wire surgical instrument that can maintain the guide wire in neutral positions.

BACKGROUND

The use of orthopedic fastening devices, such as bone screws, has greatly aided the medical field in the treatment of bone fractures, as well as enabling the ever increasing use of orthopedic implants and orthopedic appliances. With respect to the treatment of bone fractures, it is sometimes desired to surgically reposition the fragmented bone members in an anatomically acceptable orientation, and then fasten the bone members together in order to facilitate the healing process. Bone screws are typically employed in stabilization procedures used to treat bone fractures.

When a bone screw is employed, either to fasten two or more members together or to secure an orthopedic appliance (e.g. bone plate) to a bone, alignment and proper orientation are critical. To ensure proper alignment, a guide wire is often installed along the desired trajectory for the bone screw. The cannulated bone screw is then disposed over the guide wire. The guide wire functions to guide the cannulated bone screw in its proper direction. After the insertion of the bone screw, the guide wire is removed from the joined components. One skilled in the art will readily appreciate that a cannulated component refers to a small diameter through-passage throughout the entire length of the component and coaxial therewith that can be configured to insert a guide wire therethrough.

Typically, a cannulated driver is used to drive the cannulated screw over the guide wire. After the cannulated screw has been deposited over the guide wire, a cannulated driver is typically positioned over the guide wire. The cannulated driver rotates the screw over the guide wire and into a bone. In previous implementations, the guide wire rotated with the cannulated driver as the screw was inserted. In other implementations, the guide wire was also inserted deeper into the bone as the screw is driven into the bone. Driving the guide wire further into an incision or further rotating the guide wire may result in unwanted soft tissue damage. It is desirable to drive the cannulated screw over the guide wire but have the guide wire neither rotate nor translate axially, with respect to its initial position.

SUMMARY

The present teachings generally include a cannulated medical instrument for insertion of a medical device over a guide wire. The cannulated medical instrument generally includes a cannulated driver member configured to engage the medical device and insert the medical device at an insertion rate. A clasping device operatively connects to the cannulated driver member. The clasping device moves the guide wire distally away from the cannulated driver member at an extraction rate upon rotation of the cannulated driver member.

In another aspect, the present teachings generally include a cannulated medical instrument for insertion of a medical device over a guide wire. The cannulated medical instrument generally includes a cannulated driver member configured to engage the medical device and insert the medical device at an insertion rate and a lead screw operatively connected to the cannulated driver member. The lead screw has an instrument thread pitch. A clasping device is configured to receive the lead screw. The clasping device moves the guide wire distally away from the cannulated driver member at an extraction rate based on at least the instrument thread when the lead screw rotates in response to rotation of the cannulated driver member.

In a further aspect, the present teachings generally include a cannulated medical instrument for insertion of a medical device over a guide wire. The cannulated medical instrument generally includes a first member configured to engage the medical device over the guide wire and insert the medical device at an insertion rate. A second member connects for rotation with the first member. A clasping device connects to the second member. The clasping device moves the guide wire distally away from the first member at an extraction rate pitch when the second member rotates in response to rotation of the first member.

In yet another aspect, the present teachings generally include a method for using a cannulated driver for driving a fastener over a guide wire. The method includes securing a clasping device connected to the guide wire and rotating the cannulated driver. The fastener is inserted into the bone upon rotation of the driver. The method further includes extracting the guide wire at an extraction rate.

In a further aspect, the present teachings include rotating the cannulated driver with a drive motor.

In another aspect, the present teachings include rotating the cannulated driver by hand.

In an additional aspect, the present teachings include rotating a thumb screw and securing the guide wire within the clasping device.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description, the appended claims, and the accompanying drawings, wherein:

DETAILED DESCRIPTION

The following description of the embodiments is merely exemplary in nature and is in no way intended to limit the invention, its application, or uses. Moreover, while the present invention is discussed below in relation to driving a bone screw, those skilled in the art will recognize that the cannulated segmented devices such as drills, reamers, buttress pins, etc. may be used. Moreover, the present invention can be used with many materials, wherein at least two materials need to be joined together.

Figure 1:
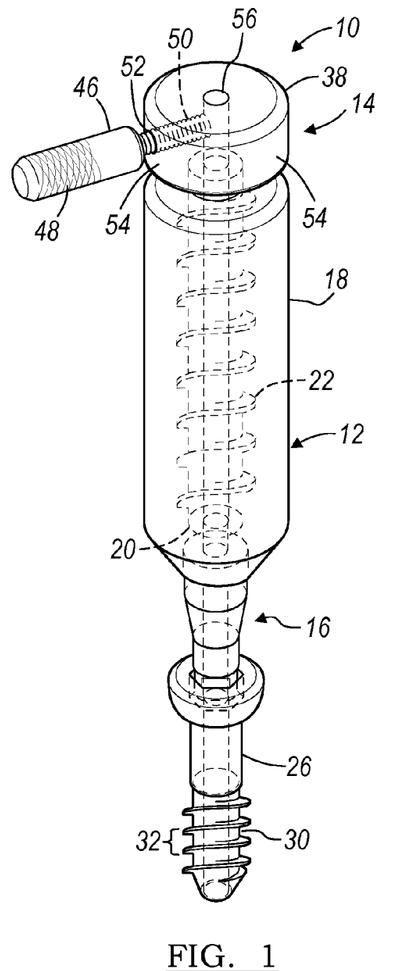
FIG. 1 is a perspective view of a guide wire retaining driver constructed in accordance with the various embodiments of the present invention.
Figure 2:
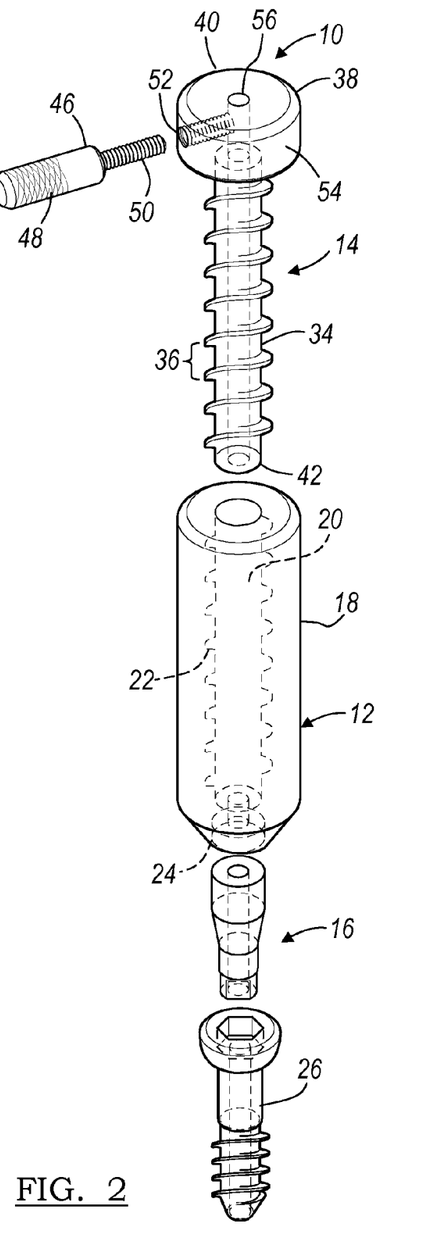
FIG. 2 is an exploded perspective view of the driver of FIG. 1 showing a driver member, a follower member, a guide wire clasping device, and an engaging member.

With reference to FIGS. 1 and 2, a guide wire retaining driver is shown generally indicated by reference numeral 10. The driver 10 includes a driver member generally indicated by reference numeral 12 and a follower member generally indicated by reference numeral 14. An engaging member which is connected to the driver member 12 is generally indicated by reference numeral 16.

The driver member 12 includes a handle portion 18 that can be used to manually rotate the driver member 12 which rotates the engaging member 16. The handle portion 18 can have flutings, knurled surfaces, or the like, which provide more traction for manual actuation. The driver member 12 also includes an internal bore 20 that includes a driver threaded portion 22 throughout at least a portion of the internal bore 20. The driver threaded portion 22 is configured to accept the follower member 14, so that the follower member 14 can be rotated into and thus at least partially disposed within the driver member 12.

The driver member 12 includes an engaging member connection point 24. In FIG. 1, the engaging member 16 is shown connected to driver member 12 at the engaging member connection point 24. In FIG. 2, the engaging member 16 is shown detached from the driver member 12. It will be appreciated that the engaging member 16 can be configured to fixedly connect to the driver member 12, or be releasably attached. As such, the engaging member 16 can be press fit into the driver member 12, or other suitable locking mechanism such as mechanical threads or chemical bonding may be used.

The engaging member 16 can be configured to engage conventional fasteners 26 with conventional heads, such as a six-sided hex-head 28, and shown in FIG. 2. It will be appreciated that many different heads may be used either on the engaging member 16 or on the conventional fasteners 26, such as Philips, hex, Torx®, slotted, or the like. Other heads may include one-direction engagement heads that only allow the engaging member 16 to insert the conventional fasteners 26 but not remove it. Other heads may use break away heads as are known in the art. Other suitable bone fixation systems and methods of use thereof are disclosed in commonly assigned U.S. Pat. Nos. 6,022,352 and 5,810,821, both to Vandewalle, issued Feb. 8, 2000 and Sep. 22, 1998, respectively, which are hereby incorporated by reference as if fully set forth herein.

The conventional fastener 26 can be a modified conventional bone screw or other such threaded fastener that is configured with a suitable head to engage with the engaging member 16. It will be appreciated that not only is the conventional fastener 26 cannulated, the driver member 12, the follower member 14, and the engaging member 16 are cannulated as well. It will also be appreciated that the driver 10 may insert other medical devices with which the engaging member can be configured to connect. Other exemplary engaging members and fasteners are disclosed in commonly assigned U.S. Pat. No. 6,402,757 issued Jun. 11, 2002, which is hereby incorporate by reference as if fully set forth herein.

The conventional fasteners 26 have a fastener threaded portion 30 with a device thread pitch 32. Depending on the device threaded pitch 32, the fastener 26 is inserted into a material at a certain depth per rotation. More specifically, fasteners 26 with a dense device thread pitch 32 will have a smaller insertion rate per rotation when compared to fasteners 26 with a larger device thread pitch 32 (i.e. less threads per inch).

The follower member 14 includes a threaded portion 34 having an instrument thread pitch 36. In the various embodiments, the follower member 14 can be configured to be threaded into the internal bore 20 of the driver member 12. While the follower member 14 can be threaded completely into the driver member 12 or completely removed therefrom, the follower member 14 remains rotateably movable throughout a plurality of positions in the driver member 12. Furthermore, the cannulated follower member 14 can be configured to remain coaxial with the cannulated driver member 12, the engaging member 16, and, if applicable, the fastener 26 throughout the plurality of positions in the driver member 12.

The follower member 14 includes a clasping device 38 connected to the following member at an end 40 distal from an insertion end 42, which is configured to insert into the member driver 12. The clasping device 38, like the follower member 14, is cannulated so that a guide wire 44 (FIG. 3) can be inserted into the clasping device 38 and through the follower member 14. The clasping device 38 can be configured to fixedly attach to the end 40 of the follower member 14. The clasping device 38 can also be releasably attached to the follower member 14, which allows varying threaded portions 34 to be attached to a single clasping device 38. As such, the clasping device 38 may be attached to the follower member 14 using a press fit, a snap fit, a threaded connection, or some other suitable releasable connection. An exemplary guide wire is disclosed in commonly assigned U.S. Pat. No. 6,402,757 already incorporated by reference.

Figure 3:
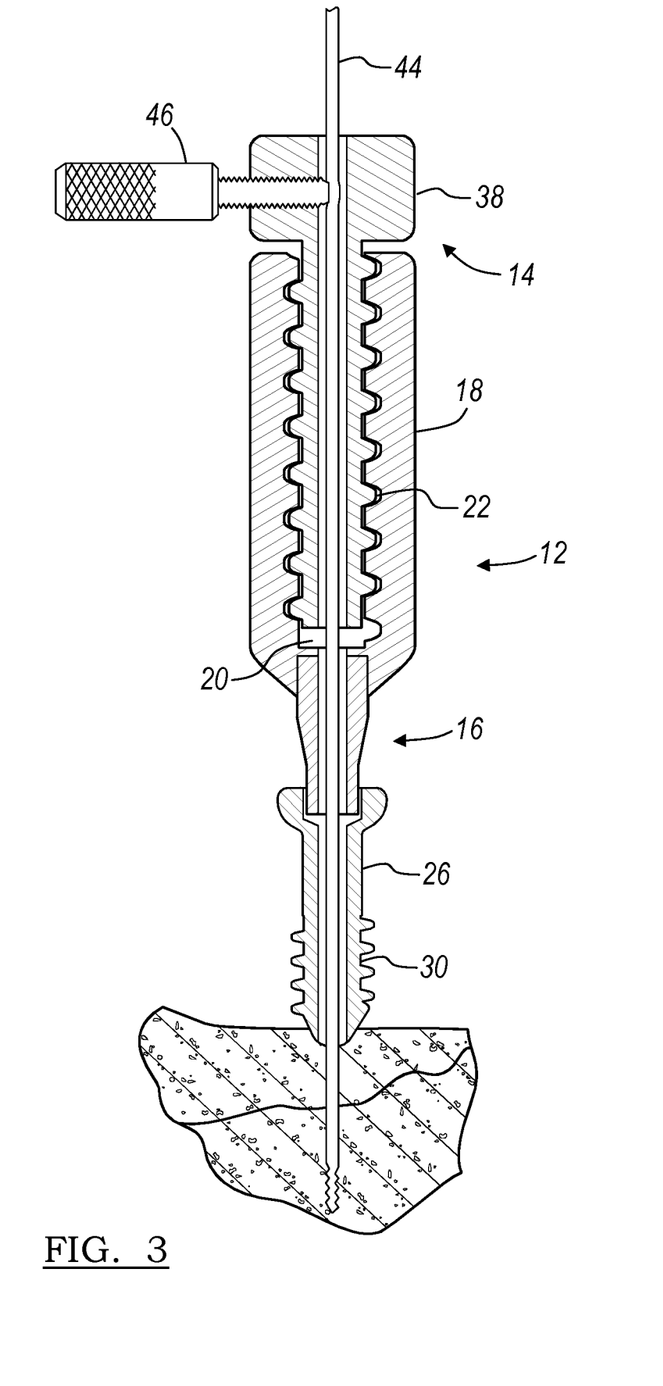
FIG. 3 is a cross sectional view of the driver of FIG. 1 showing an internal pathway of a guide wire through the driver, which is shown slightly inserted into a material, such as a bone.

A thumbscrew 46 can be connected to the clasping device 38. The thumbscrew 46 can be configured to be threaded into the clasping device 38, such that tightening the thumbscrew 46 secures the guide wire 44 within the clasping device 38, as shown in FIG. 3. It will be appreciated that the thumbscrew 46 may be configured in different ways to ultimately apply a force against the guide wire 44 (FIG. 3) to secure it within the clasping device 38 or any other clasping device 38 may be used to secure the guide wire 44.

In the various embodiments, the thumbscrew 46 has a knurled portion 48 and a thumbscrew threaded portion 50. The clasping device 38 has a threaded aperture 52 configured to receive the thumbscrew threaded portion 50. The threaded aperture 52 is open to an exterior surface 54 and a clasping device internal bore 56. As such, a user (not shown) can rotate the thumbscrew 46 into the threaded aperture 52 and secure the thumbscrew 46 against the guide wire 44 in the clasping device 38.

With reference to FIG. 3, the guide wire 44 is shown inserted through the cannulated driver 10. The thumbscrew 46 is shown tightened against the guide wire 44, thus securing it within the follower member 14. The driver 10 is shown connected to a fastener 26 positioned over the guide wire 44 both of which are partially inserted into bone material 58.

Figures 4, 5:
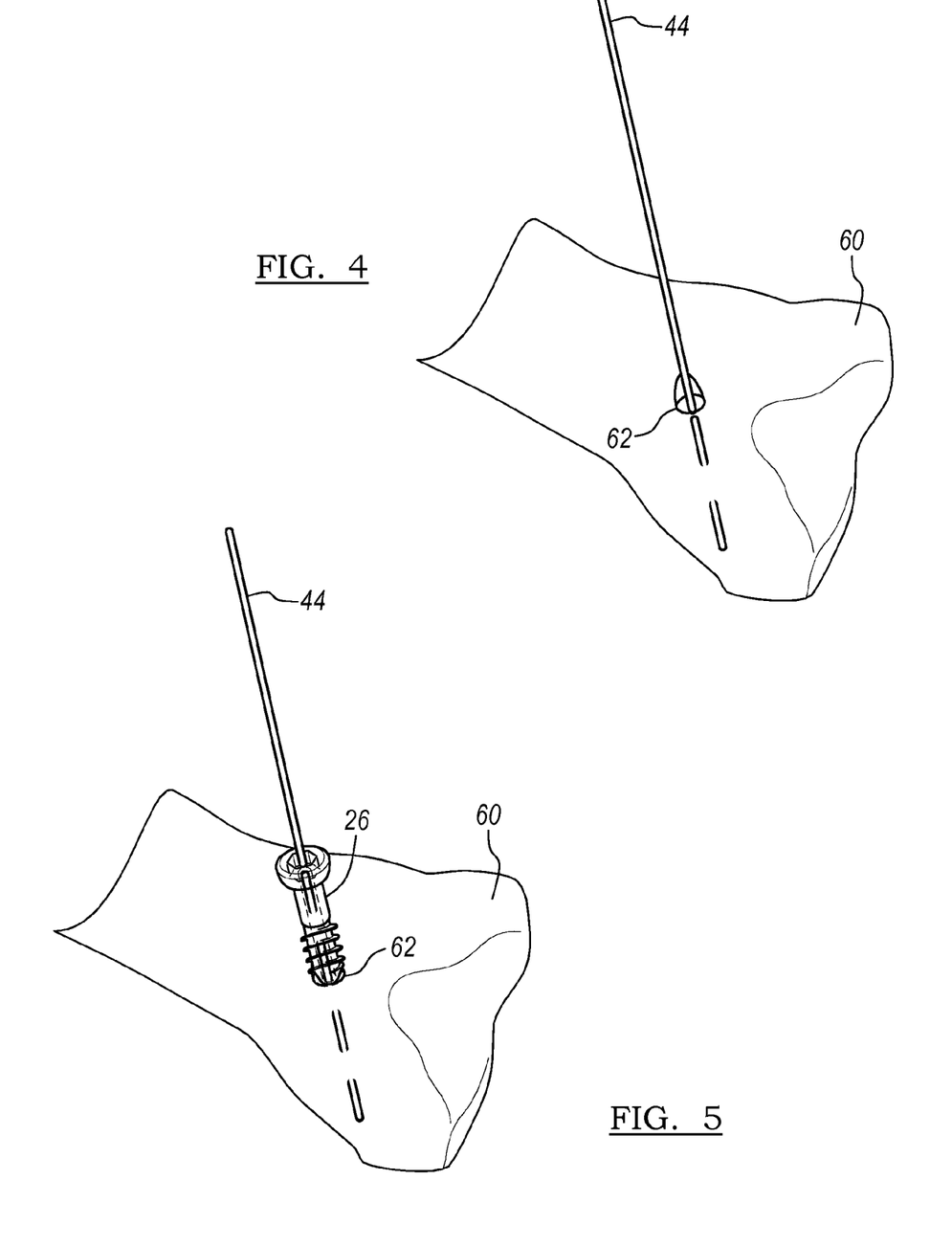
FIG. 4 is a perspective view of the guide wire inserted into the bone.
FIG. 5 is a perspective view of a cannulated bone screw inserted over the guide wire, both of which are slightly inserted into the bone.

With reference to FIG. 4, the guide wire 44 is shown partially inserted into an exemplary femoral section 60. It will be appreciated that the guide wire retaining driver 10 can be used with various bones, or for the specific use of affixing femoral neck fractures. It will, nevertheless, be appreciated that the driver 10 can be used with various bones of the human body or other applicable skeletal structures. It will also be appreciated that the driver 10 may be used outside the realm of medical devices to assist in affixing at least two pieces of material together. If used in such a non-medical environment, some characteristics that rendered the driver 10 suitable for use with medical devices need not be implemented on the driver 10 outside the medical realm.

Insertion of the guide wire 44 into the femoral section 60, as shown in FIG. 4, is an exemplary step in the method of using the driver 10. As such, a small cavity 62 is prepared in the femoral section 60 using a drilling device, or the driver 10 outfitted with a drill member (not shown). The guide wire 44 is inserted into the cavity 62. It should be appreciated that the guide wire 44 may be configured with a burr (not shown), which allows a user (not shown) to create the cavity 62 using the guide wire 44 in lieu of, or along with, the drilling device.

Figures 6, 7:
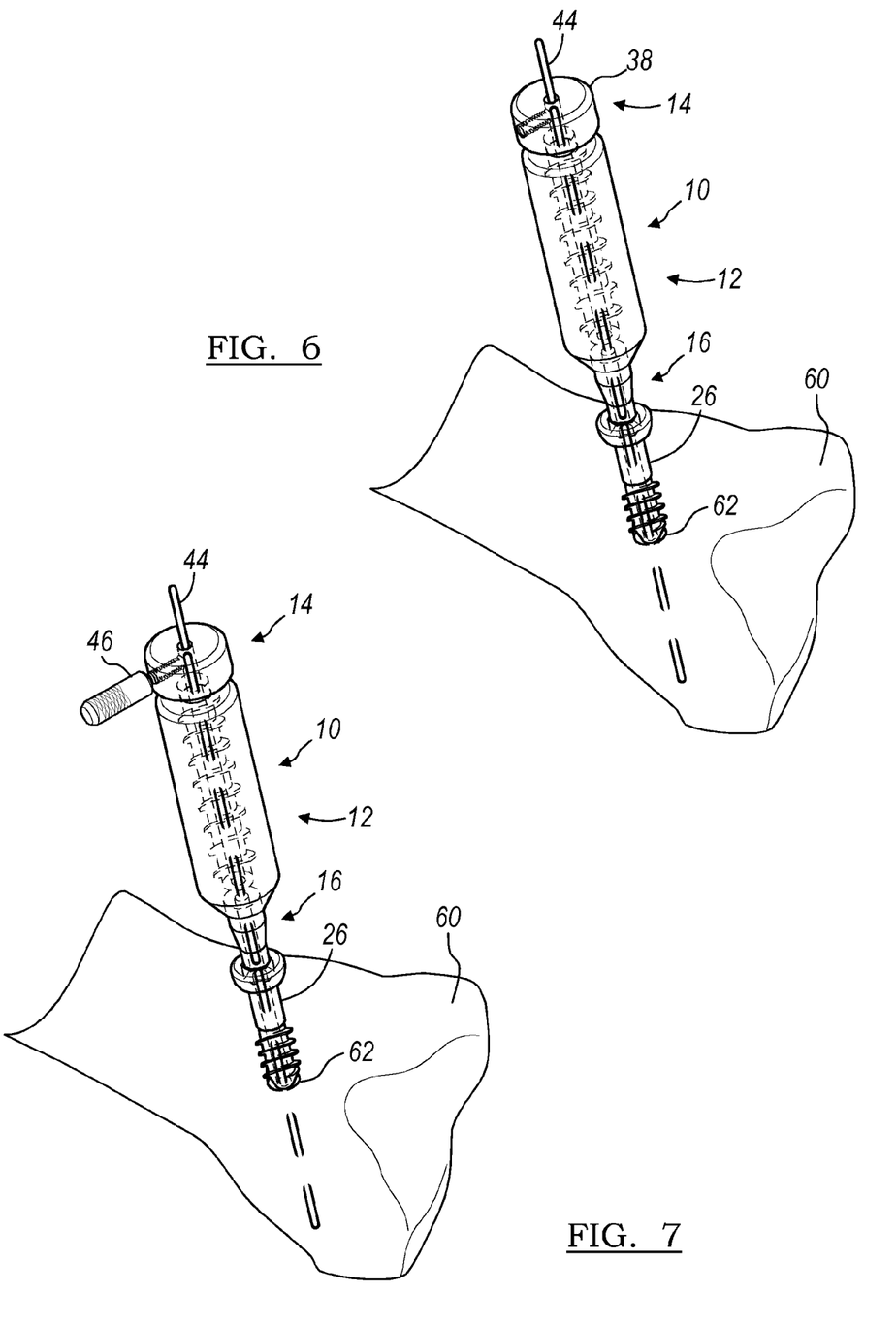
FIG. 6 is a perspective view of the guide wire retaining driver of FIG. 1 inserted over the guide wire and engaged to the bone screw.
FIG. 7 is a perspective view of the guide wire retaining driver of FIG. 6 showing a thumbscrew inserted into a guide wire clasping device to retain the guide wire.

With reference to FIGS. 5, 6, and 7, the fastener 26 is shown initially positioned over the guide wire 44 and slightly inserted into the femoral section 60, as shown in FIG. 5. The driver 10 is then inserted over the guide wire 44 and engaged with the fastener 26, as shown in FIG. 6. The thumbscrew 46 is then inserted into the clasping devices 38 and secured against the guide wire 44, as shown in FIG. 7. It will be appreciated that a progression from FIG. 4 through FIG. 7 illustrates a method of use of the driver 10. It will be further appreciated that the driver 10 can be set up in many different ways, such that the driver 10 and the fastener 26 in combination can be positioned over the guide wire 44. Furthermore, the guide wire 44 need not be used with the driver 10, such that the fastener 26 can be inserted without the guidance of the guide wire 44.

Figure 8:
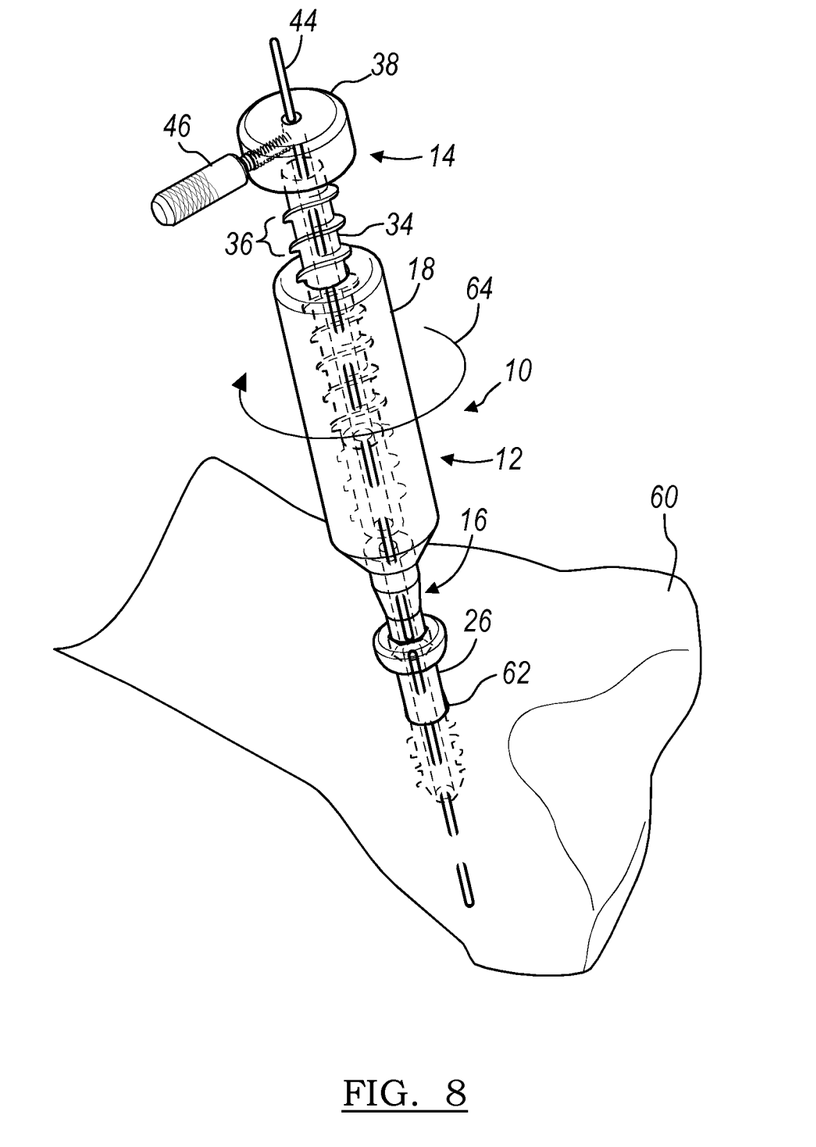
FIG. 8 is a perspective view of the guide wire clasping device of FIG. 6 showing rotation of the driver member and insertion of the bone screw, while the follower member remains in a neutral position.

With reference to FIG. 8, the driver member 12 is shown being rotated in a clockwise motion, as noted by reference numeral 64. It will be appreciated that as the driver member 12 rotates the fastener 26 is driven deeper into the femoral section 60. As the fastener 26 progresses deeper into the femoral section 60, the driver member 12 rotates around the threaded portion 34 of the follower member 14. It will be appreciated that the follower member 14 can remain in the same position as the driver member 12 rotates the fastener 26 deeper into the femoral section 60. Because the follower member 14 remains in the same position, the guide wire 44 neither rotates nor moves axially with the driver member 12 as it inserts the fastener 26.

As noted earlier, the fastener 26 has the threaded portion 30 with the device thread pitch 32. The follower member 14 also has a threaded portion 34 with an instrument thread pitch 36. If the device thread pitch 32 is about equal to the instrument thread pitch 36, the distance between the clasping device 38 and the driver member 12 will be about equal to the distance the fastener 26 has been driven into the femoral section 60. More specifically, an insertion rate of the fastener 26 will be about equal to an extraction rate of the guide wire 44. If you insert the fastener about one inch (about 2.5 centimeters), the guide wire 44 will be extracted about one inch (about 2.5 centimeters), which, therefore, maintains the guide wire 44 at its initial or neutral position. With the two thread pitches 32 and 36 equal, the follower member 14 will not translate axially, with respect to its initial position, so that the guide wire 44 neither rotates nor moves axially, thereby preventing the guide wire 44 from being driven deeper into the patient.

It will be appreciated that differences in either the device thread pitch 32 or the instrument thread pitch 36 will cause the follower member 14 to translate axially either away from or toward the fastener 26. As such, the extraction rate of the guide wire 44 can be altered to be greater or less than the insertion rate of the fastener 26. Furthermore, the follower member 14 can be altered to translate toward the driver member 12 as the driver member 12 inserts the fastener 26, except that the follower member 14 would need to be at least partially extended from the driver member 12 as shown in FIG. 8.

Figure 9:
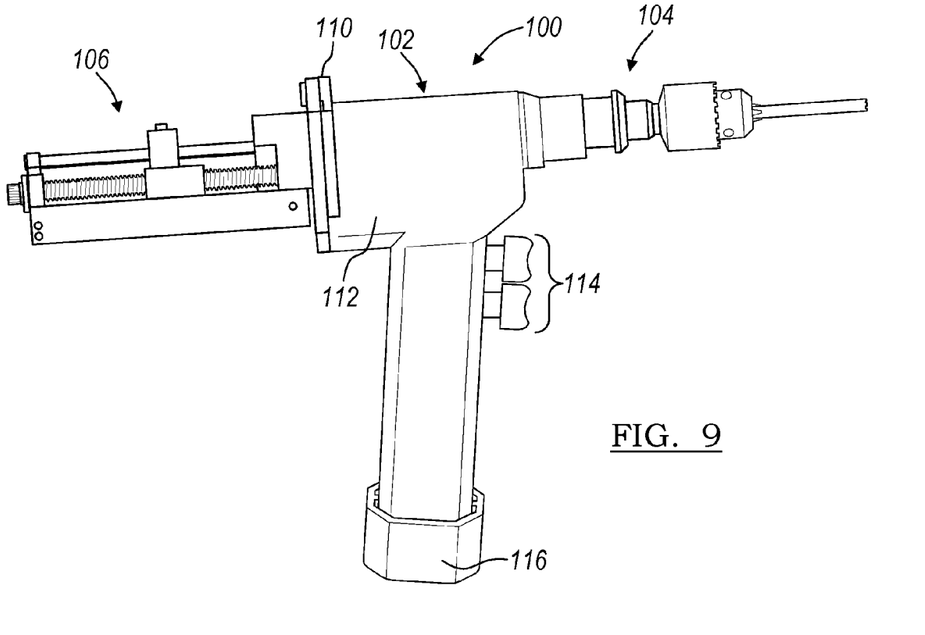
FIG. 9 is a side view of the guide wire retaining driver constructed in accordance with the various embodiments of the present invention showing a modified powered driver member, engaging member, and a guide wire clasping rear assembly.

With reference to FIG. 9, a guide wire retaining driver is shown constructed in accordance with various embodiments of the present invention and generally indicated by reference numeral 100. It will be appreciated that the driver 100 can also maintain the guide wire 44 (FIG. 8) so that it neither rotates nor moves axially with respect to the guide wire 44. To that end, the driver 100 includes a modified conventional power driver generally indicated by reference numeral 102. The power driver 102 is connected to a driver member and a rear assembly generally indicated by reference numerals 104 and 106, respectively.

It will be appreciated that the power driver 102 is cannulated so that the guide wire 108 (FIGS. 13 and 14) is similar, if not identical to the guide wire 44, can be positioned through the driver member 104, the power driver 102, and the rear assembly 106. It will be further appreciated that there are many suitable power drivers available that are both cannulated and suitable as a medical device. One exemplary modifiable power driver is commercially available from Aesculap® (Center Valley, Pa.) under the trade name Acculan® drill.

The powered driver 102 includes a modified backplate 110 connected to a rechargeable driver body 112. The rechargeable driver body 112 has speed and direction controls 114 and a battery cap 116. The direction controls 114 are configured so that the driver body 112 can operate in forward and in reverse and at variable speeds commensurate with the position of the direction controls 114. The battery cap 116 secures a rechargeable battery (not shown) within the driver body 112.

Figure 12:
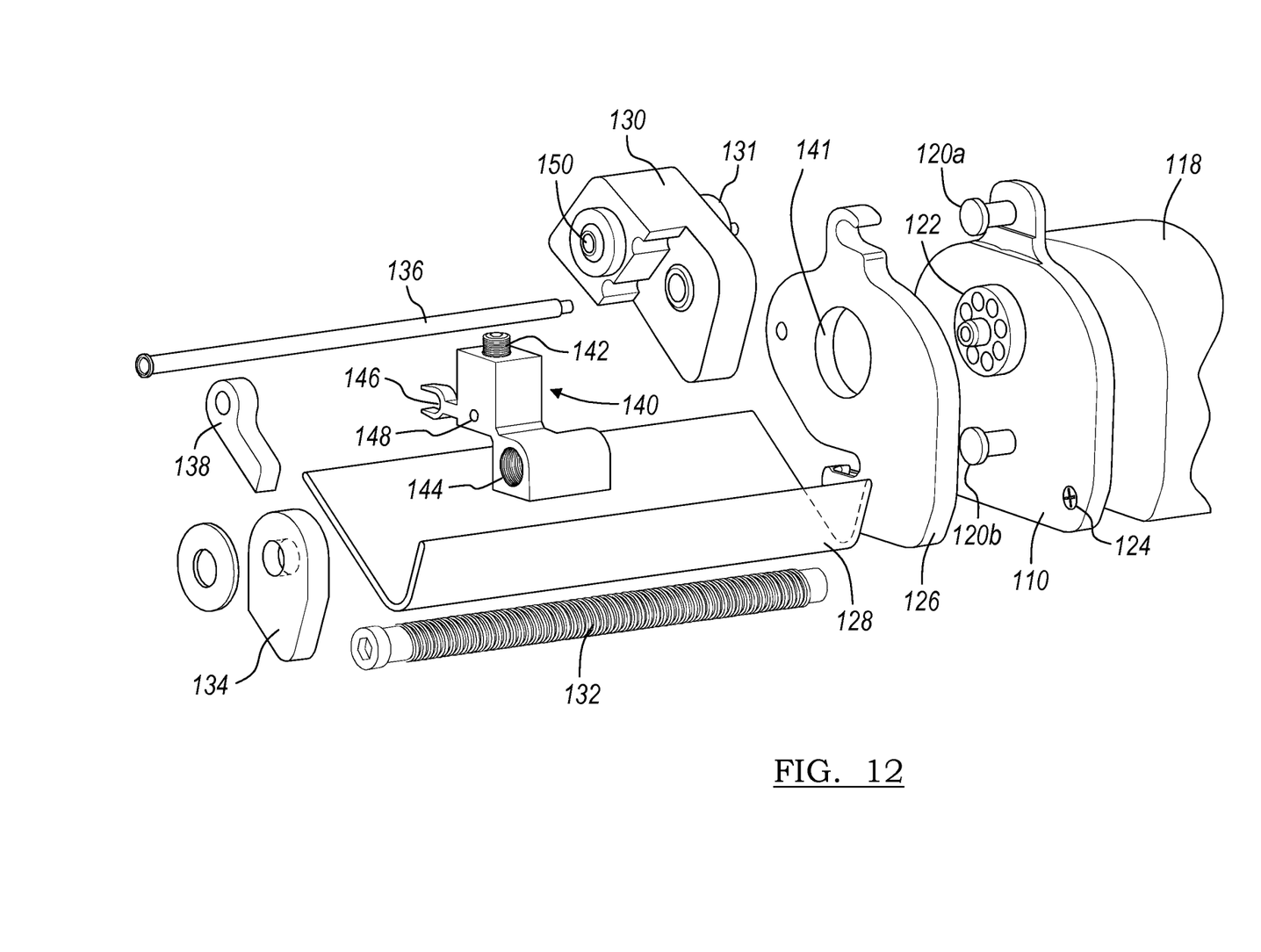
FIG. 12 is an exploded perspective view of the rear assembly of FIG. 11.

The modified backplate 110 connects to a rear portion 118 of the driver body 112. As shown in FIG. 12, the modified backplate 110 includes a first post 120a and a second post 120b, collectively referred to hereinafter as rear posts 120. The modified backplate 110 also includes an engaging wheel 122 that is coaxial with the driving member 104. The modified backplate 110 can be connected to the rear portion 118 of the driver body 112 with suitable mechanical fasteners 124, or other such suitable forms of bonding such as but not limited to welding or adhesives.

Figure 10:
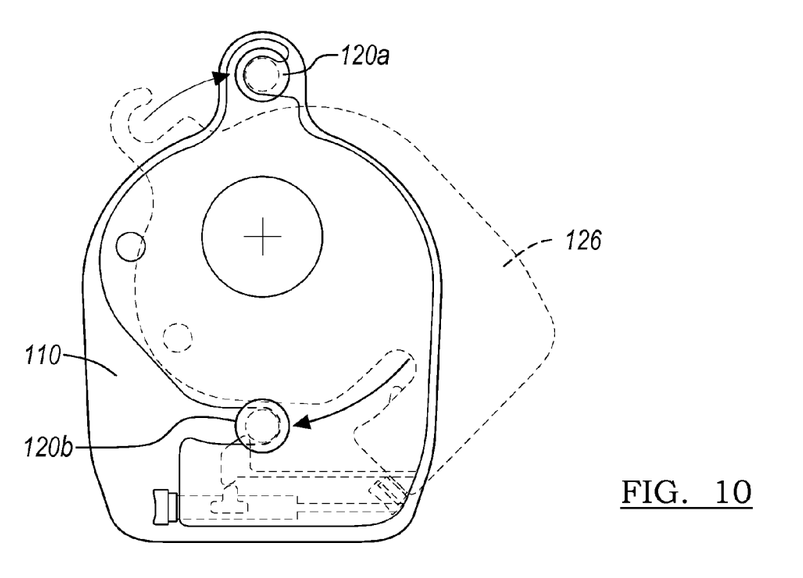
FIG. 10 is a rear view of the modified powered driver member showing a rear mounting plate that connects with the rear assembly.

With reference to FIGS. 10 and 12, the rear assembly 106 connects to the modified backplate 110 by placing a mounting plate 126 of the rear assembly 106 in line with the modified backplate 110 and abutting it at a slightly canted angle. For example, as shown in FIG. 10, the mounting plate 126 is shown slightly canted angle such that the connector plate 126 is canted counterclockwise with respect to the to the backplate 110. After abutting the mounting plate 126 to the backplate 110, the rear assembly 106 is rotated clockwise into vertical alignment with respect to the backplate 110. Upon achieving vertical alignment, the mounting plate 126 locks into the rear posts 120 of the power driver 102.

Figure 11:
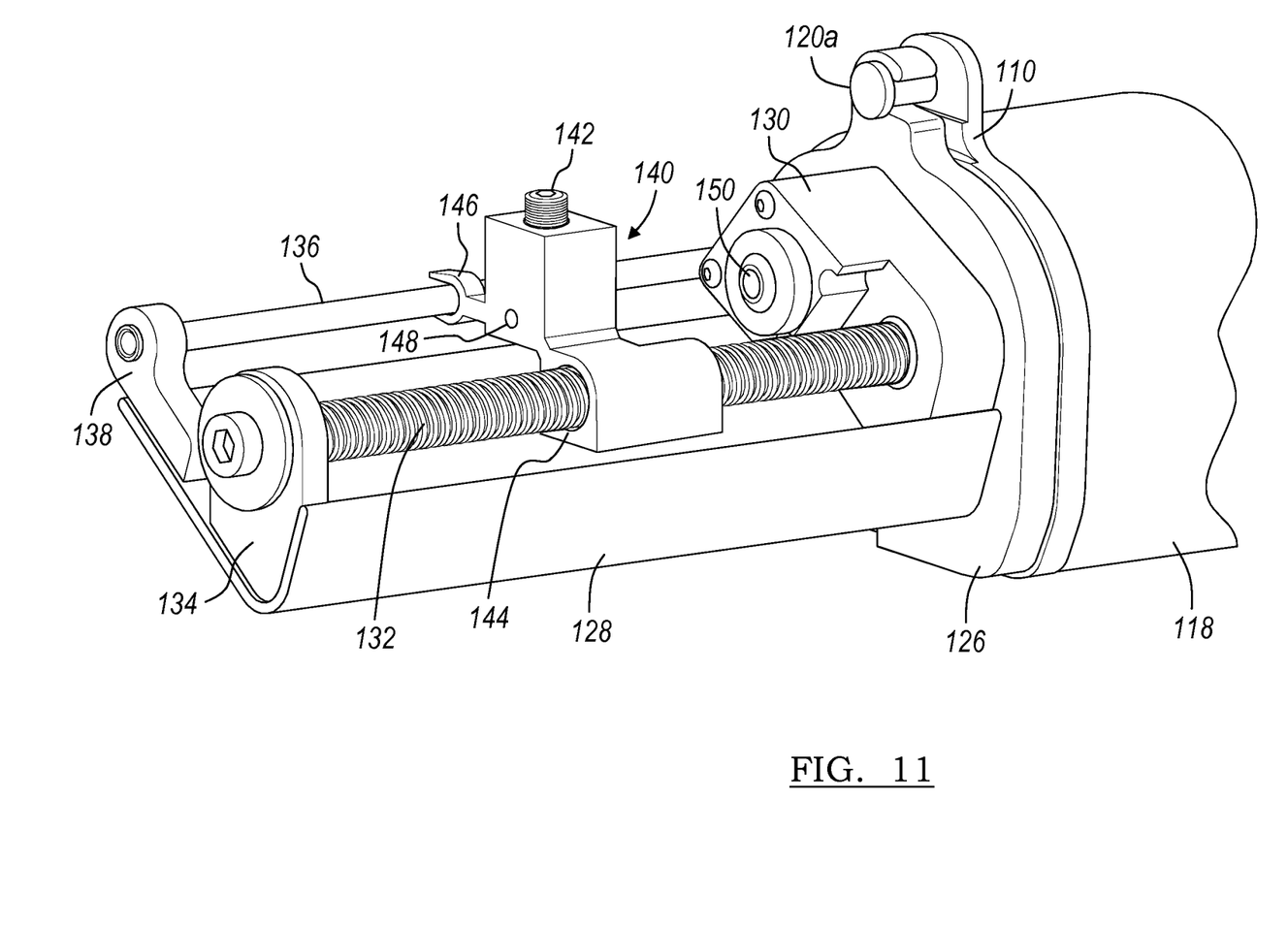
FIG. 11 is a perspective view of the rear assembly showing a gearbox, a lead screw, and a guide wire clasping device.

With reference to FIGS. 11 and 12, the rear assembly 106 includes an assembly pan 128 connected to a drivetrain 130. A lead screw 132 connects the drivetrain 130 to a rear bracket 134. A shaft 136 connects a flange 138 to the mounting plate 126. Both the drivetrain 130 and the assembly pan 128 are connected to the mounting plate 126. The rear bracket 134 and the flange 138 are connected to the assembly pan 128 at a location distal to the drivetrain 130. A guide wire clasping device 140 is rotateably engaged to the lead screw 132 and coupled with the shaft 136.

The drivetrain 130 is connected to the mounting plate 126 so that a drive wheel 131 is disposed in a mounting plate aperture 141 (FIG. 12). When the mounting plate 126 is connected to the backplate 110, the drive wheel 131 connects with the engaging wheel 122 thereby delivering rotational power from the power driver 102 to the drivetrain 130. The drivetrain rotateably connects the engaging wheel 122 to the lead screw 132 so that rotation of the engaging wheel 122 rotates the lead screw 132. In the various embodiments, there is no gear reduction in the drivetrain 130, such that the engaging wheel 122 rotates at the same speed as the lead screw 132. It will be appreciated that the drivetrain 130 can incorporate additional gearing so that the lead screw 132 is rotated at different but proportional speed to the driver 102. Moreover, the drivetrain 130 can be configured where the gear ratio is adjustable and the ratio of driver 102 rotation speed to lead screw 132 rotation speeds can be altered in situ.

Figures 13, 14:
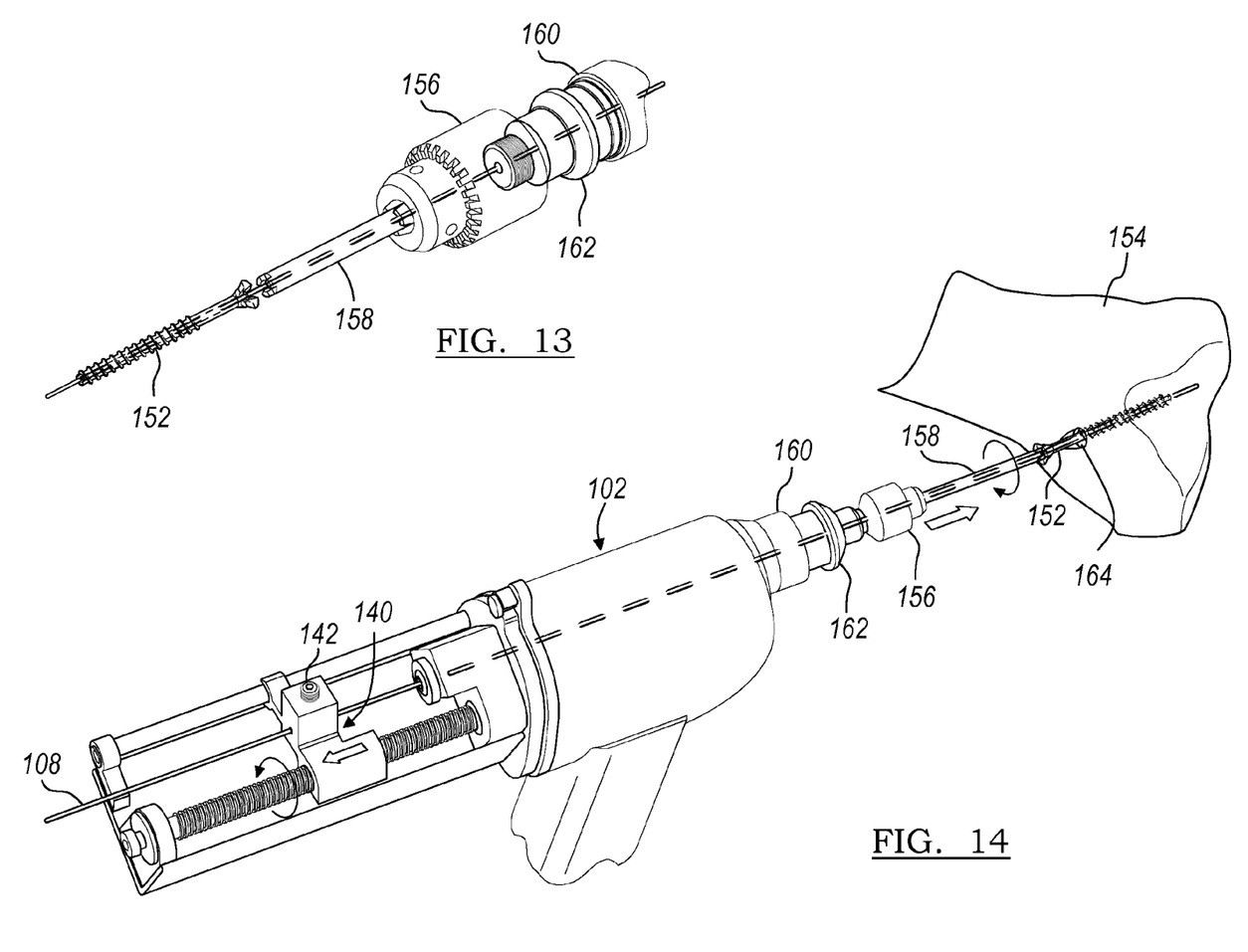
FIG. 13 is a detailed view of the engaging member showing the guide wire through the engaging member and the bone screw.
FIG. 14 is a perspective view of the guide wire retaining driver of FIG. 9 showing the driver inserting the bone screw while maintaining the guide wire at a neutral position.

With respect to FIG. 11 and FIG. 14, the guide wire clasping device 140 includes a setscrew 142, a lead screw channel 144, and a shaft follower 146. Below the setscrew 142 is a guide wire pass-through 148. The guide wire 108 (FIG. 14) is passed through a guide wire aperture 150 in the drivetrain 130 and then through the guide wire pass-through 148 in the guide wire clasping device 140. The setscrew 142 is rotated into the guide wire clasping device 140 to secure the guide wire 108.

With the guide wire 108 secured in the guide wire clasping device 140, the guide wire 108 will move with the guide wire clasping device 140 when the lead screw 132 rotates. As such, the power driver 102 rotates, which drives the drivetrain 130 that, in turn, rotates the lead screw 132. The lead screw channel 144 is configured so that the guide wire clasping device 140 translates away from the driver 102 as the driver 102 drives the fastener 152 into a bone 154, as depicted in FIG. 14.

With reference to FIG. 9 and FIG. 13, the driver member of the driver 100 includes a removable modified chuck 156 and an engaging member 158 that is configured to engage various fasteners 152, of fasteners 26 as discussed above. The chuck 156 is a modified chuck, an example of which is commercially available from Jacobson® through various commercial vendors. Attached to the rear portion of the chuck 156 is a mounting sleeve 160 that mounts the chuck 156 to the power driver 102. Pushing a mounting sleeve lip 162, away from the power driver 102 will detach the chuck 156 and the mounting sleeve 160 from the power driver 102. It will be appreciated that the chuck 156 can attached to the mounting sleeve 160 with mechanical threads 164 or other forms of suitable bonding. As such, the chuck 156 and the mounting sleeve 160 may be releasably attached to the power driver 102 or fixedly attached.

With reference to FIG. 14, the components of the driver 100 are assembled and used to insert a fastener 152 into the bone 154. The guide wire 108 is inserted into the bone 154. A cavity 164 can be created in the bone 154 prior to insertion of the guide 108, or can be created with the guide wire 108, as discussed above, with reference to the guide wire 44. The fastener 152 is positioned over the guide wire 108. The driver 100 is positioned over the guide wire 108 and engaged to the fastener 152. The guide wire 108 is locked in the guide wire clasping device 140 with the setscrew 142. As the driver 100 inserts the fastener 152 into the bone 154, the guide wire clasping device 140 is configured to maintain the guide wire at its initial position so that the guide wire 108 neither rotates nor translates axially with respect to its initial position. It will be appreciated that once the guide wire clasping device 140 reaches either end of the lead screw 132, the lead screw channel is disengaged with the lead screw 132. The lead screw channel 144 can also be manually disengaged from the lead screw 132 and move about the lead screw 132.

In the various embodiments, the driver 100 is configured so that the extraction rate of the guide wire 108 is about equal to the insertion rate of the fastener 152. The extraction rate of the guide wire refers to the movement of the guide wire clasping device 140 so that it maintains the guide wire 108 in its initial position. It will be appreciated that as the fastener 152 is inserted the guide wire 108 does not continue in deeper with the guide wire 108, but remains in its initial position. In this case, the extraction rate and the insertion rates are equal.

Figure 15:
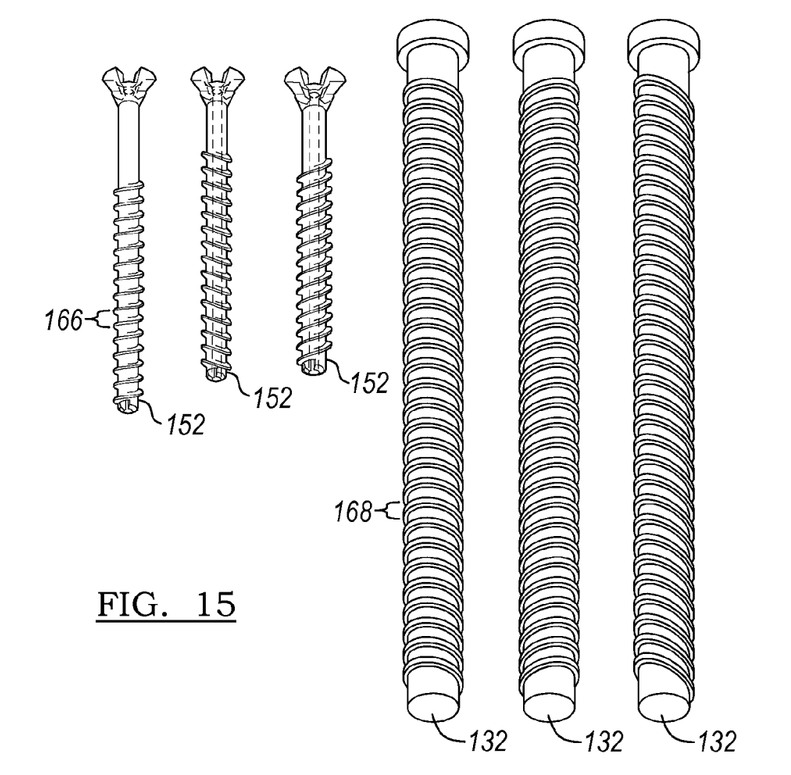
FIG. 15 is a detailed view of three exemplary lead screws and three exemplary bone screws.
Figure 16:
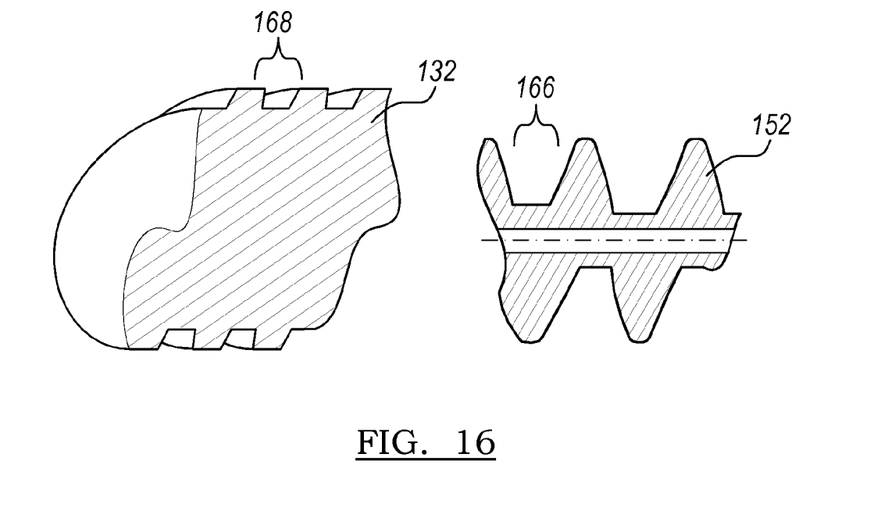
FIG. 16 is a detailed view of a pitch of the threads of the lead screw and the bone screw.

With reference to FIGS. 15 and 16, multiple lead screws 132 are shown along with multiple fasteners 152. If the drivetrain 130 has no gear reduction and the extraction rate and the insertion rate are about equal, a fastener thread pitch 166 and a lead screw thread pitch 168 are about equal. As discussed above, it will be appreciated that altering the fastener or lead screw thread pitch 166 and 168 can alter the extraction rate when compared to the insertion rate of the fastener 152. The drivetrain 130 gearing can also be altered to produce the same effect. It follows, therefore, that many lead screws and many fasteners are available with the driver 100 so that extraction rates and insertion rates can be matched or mismatched accordingly.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A cannulated medical instrument for insertion of a medical device over a guide wire comprising: a cannulated driver member configured to engage the medical device and insert the medical device at an insertion rate; a lead screw operatively connected to said cannulated driver member, said lead screw having an instrument thread pitch; a clasping device that is configured to receive said lead screw, said clasping device moves the guide wire distally away from said cannulated driver member at an extraction rate based on at least said instrument thread pitch when said lead screw rotates in response to rotation of said cannulated driver member; wherein said extraction rate of the guide wire is based on gearing between said lead screw and said cannulated driver member.

2. The cannulated medical instrument of claim 1, wherein the medical device is at least partially threaded with a device thread pitch and is configured to be inserted at said insertion rate, wherein said extraction rate of the guide wire is based on said device thread pitch and said instrument thread pitch.

3. A cannulated medical instrument for insertion of a medical device over a guide wire comprising: a first member configured to engage the medical device over the guide wire and insert the medical device at an insertion rate; a second member connected for rotation with said first member; a clasping device connected to said second member and the guide wire, said second member is operable to move said clasping device when said second member rotates in response to rotation of said first member to pull the guide wire from its initial position and distally away from said first member; and gearing connected between a lead screw and said first member so that said second member rotates in response to rotation of said first member.

4. The cannulated medical instrument of claim 3, wherein said clasping device receives said lead screw so that when said second member rotates in response to rotation of said first member said second member is operable to move said clasping device along said lead screw away from said first member.

5. The cannulated medical instrument of claim 3, wherein said second member is a follower member rotatably connected to said first member, wherein said first member and said second member receives the guide wire and wherein a portion of said second member is received within a portion of said first member.

6. A cannulated medical instrument for insertion of a medical device over a guide wire comprising: a cannulated driver member configured to engage the medical device and insert the medical device at an insertion rate; a lead screw operatively connected to said cannulated driver member, said lead screw having an instrument thread pitch; and a clasping device that translates relative to said lead screw in response to rotation of said lead screw through said clasping device; wherein said cannulated driver member rotates to insert the medical device and rotate said lead screw to cause said clasping device to move the guide wire from its neutral position and distally away from said cannulated driver member at an extraction rate that is based on a combination of said instrument thread pitch of said lead screw and said insertion rate of the medical device; wherein said extraction rate of the guide wire is based on gearing between said lead screw and said cannulated driver member.

7. The cannulated medical instrument of claim 6, further comprising a cannulated engaging member that is connected to said cannulated driver member and configured to engage the medical device.

8. The cannulated medical instrument of claim 6, wherein the medical device is at least partially threaded with a device thread pitch and is configured to be inserted at said insertion rate that is about equal to said extraction rate when said instrument thread pitch of said lead screw is about equal to said device thread pitch of the medical device.

9. The cannulated medical instrument of claim 6, wherein the medical device is at least partially threaded with a device thread pitch and is configured to be inserted at said insertion rate that is different than said extraction rate when said instrument thread pitch of said lead screw is different than said device thread pitch of the medical device.

10. The cannulated medical instrument of claim 6, wherein said clasping device holds the guide wire rotationless when the cannulated driver member rotates.

11. The cannulated medical instrument of claim 6, wherein the cannulated driver member is connected to a drive motor that drives said lead screw and said cannulated driver member.

12. A cannulated medical instrument for insertion of a medical device over a guide wire comprising: a cannulated driver member configured to engage the medical device and insert the medical device at an insertion rate; a lead screw operatively connected to said cannulated driver member, said lead screw operable to rotate when said cannulated driver member rotates; and a clasping device in which said lead screw rotates to move said clasping device along said lead screw, wherein said clasping device is operable to move the guide wire from its initial position in a direction away from said cannulated driver member at an extraction rate based on at least said instrument thread pitch when said lead screw rotates in response to rotation of said cannulated driver member; wherein said extraction rate of the guide wire is based on gearing between said lead screw and said cannulated driver member.

13. The cannulated medical instrument of claim 12, wherein said cannulated driver member and said lead screw are spaced from where the medical device is being inserted.

14. The cannulated medical instrument of claim 1, wherein said cannulated driver member and said lead screw are spaced from where the medical device is inserted when said lead screw rotates in response to rotation of said cannulated driver member.

15. The cannulated medical instrument of claim 3, wherein said first member and said second member are spaced from a location into where the medical device is being inserted.

16. The cannulated medical instrument of claim 12 further comprising a cannulated engaging member that is connected to said cannulated driver member and configured to engage the medical device.

17. The cannulated medical instrument of claim 12, wherein the medical device is at least partially threaded with a device thread pitch and is configured to be inserted at said insertion rate that is different than said extraction rate when said instrument thread pitch of said lead screw is different than said device thread pitch of the medical device.

18. The cannulated medical instrument of claim 12, wherein said clasping device holds the guide wire rotationless when the cannulated driver member rotates.

19. The cannulated medical instrument of claim 12, wherein the cannulated driver member is connected to a drive motor that drives said lead screw and said cannulated driver member.

20. A cannulated medical instrument for insertion of a medical device over a guide wire comprising: a cannulated driver member configured to engage the medical device and insert the medical device at an insertion rate; a lead screw operatively connected to said cannulated driver member, said lead screw operable to rotate when said cannulated driver member rotates; and a clasping device through which said lead screw rotates to move said clasping device with the guide wire along said lead screw in a direction away from said cannulated driver member, wherein said cannulated driver member and said lead screw are spaced from a location into where the medical device is being inserted; wherein an extraction rate of the guide wire is based on gearing between said lead screw and said cannulated driver member.

21. The cannulated medical instrument of claim 20 further comprising a cannulated engaging member that is connected to said cannulated driver member and configured to engage the medical device, said cannulated engaging member is spaced from where the medical device is inserted when said lead screw rotates in response to rotation of said cannulated driver member.

22. The cannulated medical instrument of claim 20, wherein the medical device is at least partially threaded with a device thread pitch and is configured to be inserted at said insertion rate that is about equal to said extraction rate when said instrument thread pitch of said lead screw is about equal to said device thread pitch of the medical device.

23. The cannulated medical instrument of claim 20, wherein the medical device is at least partially threaded with a device thread pitch and is configured to be inserted at said insertion rate that is different than said extraction rate when said instrument thread pitch of said lead screw is different than said device thread pitch of the medical device.

24. The cannulated medical instrument of claim 20, wherein said clasping device holds the guide wire rotationless when the cannulated driver member rotates.

25. The cannulated medical instrument of claim 20, wherein the cannulated driver member is connected to a drive motor that drives said lead screw and said cannulated driver member.

\* \* \* \* \*